(12) United States Patent
Jensen

(10) Patent No.: US 6,174,544 B1
(45) Date of Patent: Jan. 16, 2001

(54) EASY-RELEASE ALGINATE WOUND HEALING DEVICE AND METHOD

(75) Inventor: Jarl B. Jensen, Nyack, NY (US)

(73) Assignee: Euromed, Inc., Northvale, NJ (US)

( * ) Notice: Under 35 U.S.C. 154(b), the term of this patent shall be extended for 0 days.

(21) Appl. No.: 09/397,379

(22) Filed: Sep. 16, 1999

(51) Int. Cl.[7] ................ A61F 13/00; A61K 9/70
(52) U.S. Cl. .................... 424/443; 424/445; 602/43; 602/45
(58) Field of Search .................... 424/443, 402; 602/43

(56) References Cited

U.S. PATENT DOCUMENTS

| | | | |
|---|---|---|---|
| 4,940,844 | 7/1990 | Blunt | 521/116 |
| 4,948,575 | 8/1990 | Cole et al. | 424/44 |
| 5,197,945 | 3/1993 | Cole et al. | 602/49 |
| 5,238,685 | 8/1993 | Wren | 424/445 |
| 5,674,524 | 10/1997 | Scherr | 424/445 |
| 5,718,916 | 2/1998 | Scherr | 424/445 |
| 5,735,812 | 4/1998 | Hardy | 602/43 |
| 5,836,970 | 11/1998 | Pandit | 606/213 |
| 5,914,125 | 6/1999 | Andrews et al. | 424/443 |
| 5,981,821 | 11/1999 | Barikosky | 602/41 |
| 5,986,164 | 11/1999 | Kershaw et al. | 602/49 |

Primary Examiner—Shelley A. Dodson
Assistant Examiner—Konata M. George
(74) Attorney, Agent, or Firm—McDonnell Boehen Hulbert & Berghoff

(57) ABSTRACT

The wound filling device and method utilizes an alginate gel that is used to fill the wound. The alginate gel is then overlain with a dressing containing alkaline salts. The alkaline salts leach out of the dressing and into the gel. After penetrating the gel, the alkaline salts initiate hardening of the gel and binding of the gel to the dressing. Therefore, this gel can be easily removed along with the dressing without the need of potentially painful and damaging rinses.

24 Claims, 2 Drawing Sheets

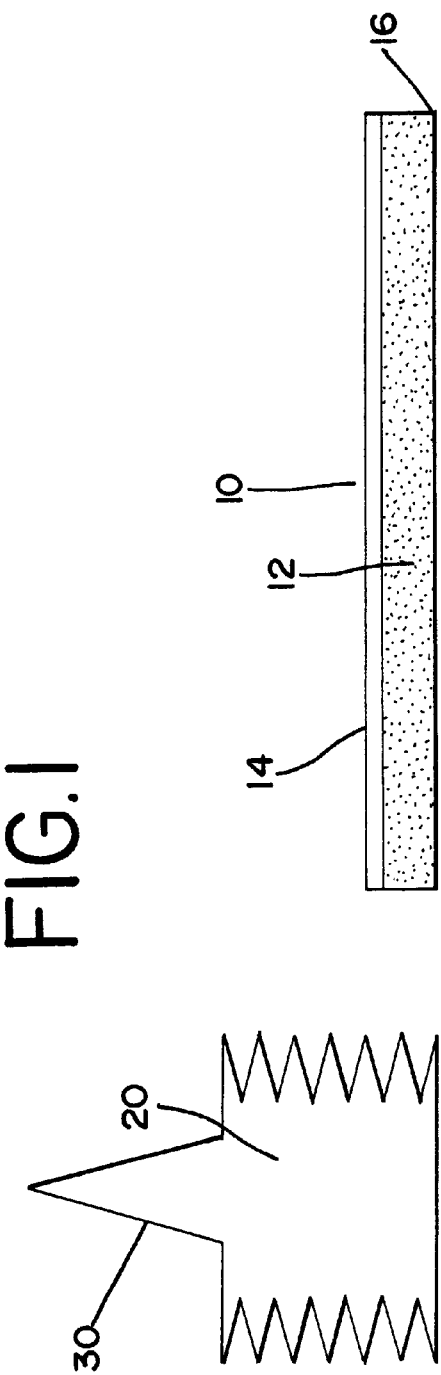
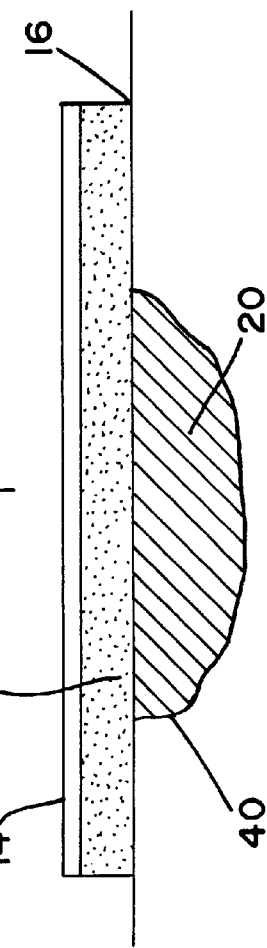

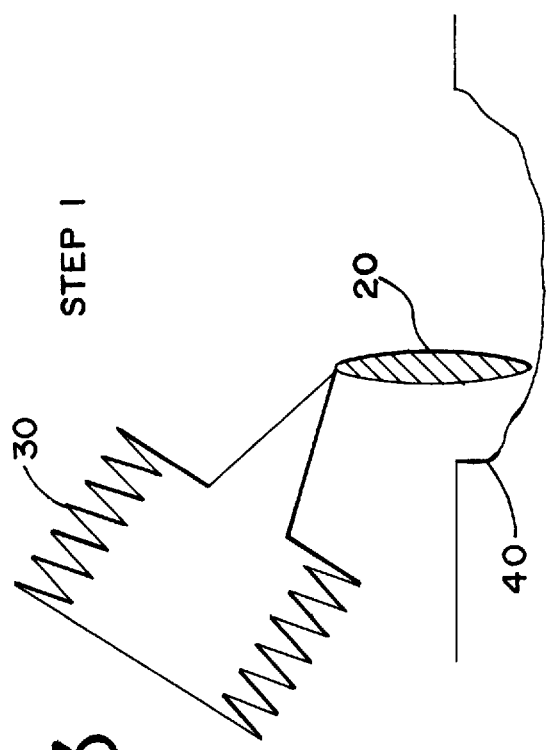
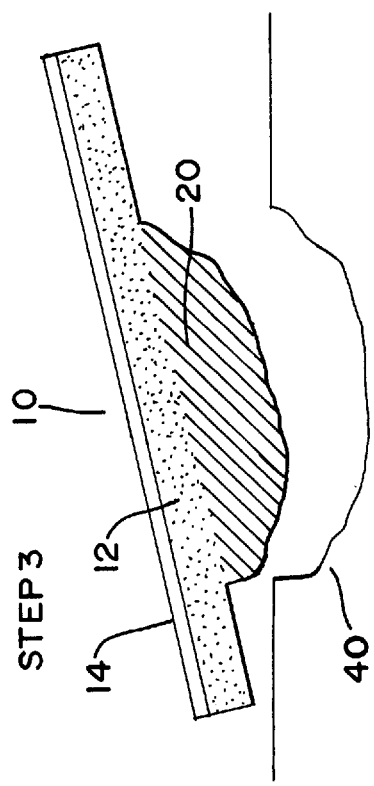
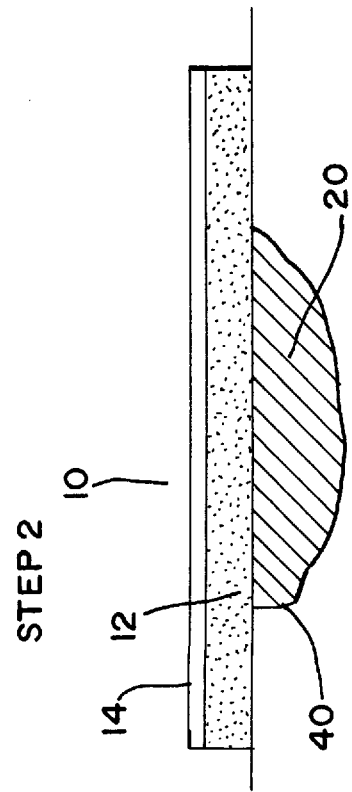
FIG. 3

EASY-RELEASE ALGINATE WOUND HEALING DEVICE AND METHOD

BACKGROUND OF THE INVENTION

1. Field of Invention

The present invention pertains to the field of wound care products and, more particularly, to wound filler and dressing combinations that are used for the treatment of wounds to the skin, such as skin ulcers and burns, as well as methods for treating such wounds.

2. Description of the Prior Art

Current injury treatment modalities consist, at least in part, of a wound dressing. Wound dressings function to seal wounds to prevent infections and function to absorb moisture from the wound in order to protect others from wound exudate. Wound dressings generally consist of flat, layered material which allow the dressing to be secured to the body effectively. Wound fillers such as foams are often applied as part of a wound dressing in order to assure tight and complete coverage of a wound site, especially for wounds where a traditional dressing would not conform well to the shape of the wound. Fillers are useful, for example, when a wound penetrates deeply beneath the skin.

Gels are effective wound fillers because their fluidity allows them to effectively seal the wound. Gels have the added benefits of reducing the risk of damage to the wound during application of the dressing and providing some soothing pain relief to the patient.

One problem with current gel fillers is that they are difficult to remove from the wound. The wound site using a gel filler may have to be irrigated with saline solutions to remove the gel. The removal process can cause discomfort to the patient, damage to the wound, and interference with the healing process.

Alginate is used in wound dressings as a way of increasing the absorbency of such dressings. Examples of alginate treatment modalities include non-woven alginate fibers, freeze dried alginate wafers, and alginate hydrogel foams.

One drawback of these alginate dressings is that they do not effectively take the shape of the wound and therefore do not provide an optimal coverage of the wound. Furthermore, they are difficult to use. The alginate fibers and wafers are difficult to apply and to remove.

There remains a need for a wound care product which is easy to apply, effectively protects the wound by taking the shape of the wound, reduces pain associated with the wound by providing a "cooling" effect, and is easily removed from the wound without the need for irrigation or other potentially damaging procedures.

SUMMARY OF THE INVENTION

The current invention overcomes the above-identified problems by providing a wound care product that contains an alginate gel that is easy to apply and effectively takes the shape of the wound, that provides a "cooling" effect to the wound site for the patient, and that slowly hardens and attaches to the wound dressing, thereby permitting efficient removal without the need for rinsing of the wound.

In the current invention, the wound is filled with an alginate gel. The alginate gel is then overlain with a dressing containing alkaline salts. The alkaline salts leach out of the dressing and into the gel. After penetrating the gel, the alkaline salts initiate hardening of the gel and binding of the gel to the dressing. The hardening of the gel and attachment of the gel to the dressing allow it to be easily removed along with the dressing.

BRIEF DESCRIPTION OF THE DRAWINGS

Presently preferred embodiments of the present invention are described below in conjunction with the drawing figures, wherein like numerals refer to like elements in the various figures, and wherein:

FIG. 1 depicts the separate components of the wound dressing according to the present invention.

FIG. 2 depicts a wound filling dressing according to the present invention after application to a wound.

FIG. 3 depicts a process for treating a wound using the present invention.

DETAILED DESCRIPTION OF THE INVENTION

FIG. 1 depicts the components of a wound healing device according to presently preferred embodiments of the present invention. The wound healing device includes a wound dressing 10 and an alginate gel filler 20 which is stored in a container 30. The wound dressing comprises a salt-containing layer 12 covered on one side by a backing film 14 and on an opposite side by one or more removable release sheets 16. The backing film 14 adds structural support to the salt-containing layer 12 and protects the side of the salt-containing layer 12 to which it is attached. The removable release sheets 16 maintain the opposite side of the salt-containing layer 12 in a sterile, protected condition.

The salt-containing layer 12 of the wound dressing 10 can be made of any medium, such as hydrocolloids, hydrogels, or foams, out of which salts can slowly dissolve and enter into the alginate. In a preferred embodiment, the salt-containing layer 12 includes a hydrocolloid adhesive. The hydrocolloid adhesive may include any water-soluble gum such as pectin, gelatin, carboxymethylcellulose, polysaccharides and the like.

The salt-containing layer 12 may include any alkaline salt such as sodium chloride, sodium sulfate, sodium carbonate, potassium chloride, calcium chloride, lithium chloride and magnesium chloride, preferably as a dihydrate. In a preferred embodiment the alkaline salt used in the salt-containing layer 12 includes calcium sulfate dihydrate, a readily available, inexpensive salt which does not cause irritation to wounds. Calcium sulfate dihydrate may be used at a concentration of 1–45% with a preferred concentration of about 10%.

An alternative salt-containing layer 12' (shown with boundary having a broken line) may be used in which a portion may extend to partially fill the wound with the alginate gel 20. Such an alternative salt-containing layer 12' may include a non-woven fabric or a gauze impregnated with the alkaline salt. The alternative salt-containing layer 12' may be advantageously used for deeper wounds.

FIG. 2 is a cross-sectional view of a wound site 40 that has been filled with the alginate gel filler 20 and covered by the wound dressing 10. The wound dressing 10 includes alkaline salts as described above and the alginate gel filler 20 capable of completely filling the wound. Although the dressing 10 and gel filler 20 in FIG. 2 may be used in any wound site 40, decubitus ulcers and burns particularly benefit from the advantages of the present invention.

FIG. 2 also shows as an alternative, the wound site 40 filled with the alternative salt-containing layer 12' (shown with boundary having a broken line) extending into the wound with the alginate gel 20.

FIG. 3 depicts a method for using the invention described in FIGS. 1 and 2. Step 1 of the method consists of dispensing an alginate gel filler 20 from a container 30 onto a wound 40 of the skin. Alternatively, the alginate gel filler 20 can be applied directly to one surface of the wound dressing 10 rather than applied directly to the wound 40. Preferably the application of the alginate gel filler 20 consists of squeezing the alginate gel filler 20 from a tube. The alginate gel filler 20 when applied to the wound 40 advantageously takes the shape of the wound 40, thereby providing an efficient barrier against the external environment. Furthermore, the alginate gel filler 20 soothes the wound 40, thereby decreasing patient discomfort. Finally, to assure easy removal of the alginate gel filler 20, the alginate gel filler 20 has the capability of hardening and binding to the wound dressing 10 when alkaline salts dissolve out of the wound dressing 10 and into the alginate gel filler 20.

Step 2 consists of applying a wound dressing 10 containing alkaline salts on top of the alginate gel filler 20. Alternatively, if step 1 consists of applying alkaline gel 20 directly to wound dressing 10, then Step 2 consists of applying the alginate gel 20 covered by the wound dressing 10 to the wound 40. Preferably, the wound dressing 10 contains a removable release sheet 16 covering the surface of the dressing that will contact the alginate gel filler 20. The release sheet is removed before applying the wound dressing 10 to the alginate gel filler 20. Step 3 is carried out within hours or days after step 2, preferably within 5 days. This provides enough time for the alkaline salts to dissolve from the dressing into the alginate gel filler 20 and to initiate hardening of the alginate gel filler 20. The alkaline salts dissolve slowly into the alginate gel filler 20 to allow the gel 20 to fill the wound 40, but initiate hardening of the gel 20 quickly enough to assure that the alginate gel 20 has hardened before the wound dressing 10 needs to be changed. As the alginate gel 20 advantageously hardens it becomes bound to the wound dressing 10. Therefore, the alginate gel filler 20 can be removed by removing the dressing 10. Further cleaning of the wound 40 to remove residual gel 20 is not necessary.

Those skilled in the art will understand that the preferred embodiments described above may be subjected to apparent modifications without departing from the true scope and spirit of the invention. Accordingly, the inventor hereby states his intention to rely upon the Doctrine of Equivalents to protect the full rights in the invention.

I claim:

1. A wound treatment device for use in treating wounds of the skin, for patients in need of such treatment, comprising, in combination:
   an alginate gel for putting into said wound, and
   a dressing comprising alkaline salt for covering said wound to contact said alginate gel, wherein said alkaline salt gradually releases from said dressing into said alginate gel after said alginate gel is placed in contact with said dressing thereby causing the alginate gel to harden.

2. The wound treatment device as set forth in claim 1, wherein said dressing comprises an outer layer and an inner layer, said inner layer further comprising hydrocolloids.

3. The wound treatment device as set forth in claim 1, wherein said alkaline salt is calcium sulfate dihydrate.

4. The wound treatment device according to claim 1, wherein said dressing comprises hydrogels.

5. The wound treatment device according to claim 1, wherein said dressing comprises hydrocolloids.

6. The wound treatment device according to claim 1, wherein said dressing comprises foams.

7. The wound treatment device according to claim 1, wherein said dressing comprises a non-woven fabric impregnated with alkaline salts.

8. The wound treatment device according to claim 7 wherein said alginate gel partially fills the wound to permit said non-woven fabric to fill the unfilled portion of the wound.

9. The wound treatment device according to claim 1 wherein said dressing comprises a gauze impregnated with alkaline salts.

10. The wound treatment device according to claim 9 wherein said alginate gel partially fills the wound to permit said gauze to fill the unfilled portion of the wound.

11. A method of treating a wound to skin tissue, said method comprising, in combination, the steps of:
   putting an alginate gel into the wound;
   applying a dressing comprising alkaline salts to said wound to contact said alginate gel;
   said alkaline salts gradually releasing out of said dressing and penetrating said alginate gel;
   said alginate gel hardening and binding to said dressing upon said penetration of said alkaline salts; and
   removing said dressing with said alginate gel attached.

12. A method according to claim 11, wherein said dressing comprises a hydrocolloid and the step of applying said dressing comprises the step of overlaying said hydrocolloid over said wound.

13. A method according to claim 11, wherein said dressing comprises a hydrogel and the step of applying said dressing comprises the step of overlaying said hydrogel over said wound.

14. A method according to claim 11, wherein said dressing comprises a foam and the step of applying said dressing comprises the step of overlaying said foam over said wound.

15. A method according to claim 11, wherein:
   said dressing comprises a non-woven fabric impregnated with said alkaline salt;
   the step of putting said alginate gel into said wound comprises the step of partially filling said wound with said alginate gel; and
   the step of applying said dressing comprises the step of inserting said non-woven fabric into said wound.

16. A method according to claim 11, wherein:
   said dressing comprises a gauze impregnated with said alkaline salt;
   the step of putting said alginate gel into said wound comprises the step of partially filling said wound with said alginate gel; and
   the step of applying said dressing comprises the step of inserting said gauze into said wound.

17. A method according to claim 11, wherein said alkaline salt is calcium sulfate dihydrate.

18. A method of treating a wound to skin tissue, said method comprising, in combination, the steps of:
   applying an alginate gel to a side of a wound dressing said side of said wound dressing comprising alkaline salts;
   contacting said alginate gel applied to said wound dressing to said wound;
   said alkaline salts gradually releasing out of said dressing and penetrating said alginate gel;
   said alginate gel hardening and binding to said dressing upon said penetration of said alkaline salts; and
   removing said dressing with said alginate gel attached.

19. A method according to claim 18, wherein said dressing comprises a hydrocolloid and the step of contacting said alginate gel applied to said wound dressing comprises the step of overlaying said hydrocolloid and alginate gel over said wound such that said alginate gel fills the wound.

20. A method according to claim 18, wherein said dressing comprises a hydrogel and the step of contacting said alginate gel applied to said wound dressing comprises the step of overlaying said hydrogel and alginate gel over said wound such that said alginate gel fills the wound.

21. A method according to claim 18, wherein said dressing comprises a foam and the step of contacting said alginate gel applied to said wound dressing comprises the step of overlaying said foam and alginate gel over said wound such that said alginate gel fills the wound.

22. A method according to claim 18, wherein:

said dressing comprises a non-woven fabric impregnated with said alkaline salt; and the step of contacting said alginate gel applied to said wound dressing comprises the step of inserting said non-woven fabric and alginate gel into said wound, said alginate gel and said non-woven fabric filling said wound.

23. A method according to claim 18, wherein:

said dressing comprises a gauze impregnated with said alkaline salt; and the step of contacting said alginate gel applied to said wound dressing comprises the step of inserting said gauze and alginate gel into said wound, said alginate gel and said gauze filling said wound.

24. A method according to claim 18, wherein said alkaline salt is calcium sulfate dihydrate.

* * * * *